United States Patent
Mundwiler et al.

(10) Patent No.: US 7,329,124 B2
(45) Date of Patent: Feb. 12, 2008

(54) INTRAOSTEAL DENTAL IMPLANT

(75) Inventors: Ulrich Mundwiler, Tenniken (CH); Marcello Memmolo, Sissach (CH); Kati Benthaus, Basel (CH)

(73) Assignee: Straumann Holding AG, Basel (CH)

( * ) Notice: Subject to any disclaimer, the term of this patent is extended or adjusted under 35 U.S.C. 154(b) by 209 days.

(21) Appl. No.: 11/087,275

(22) Filed: Mar. 23, 2005

(65) Prior Publication Data
US 2005/0233282 A1  Oct. 20, 2005

(30) Foreign Application Priority Data
Mar. 25, 2004  (EP)  .................. 04007245

(51) Int. Cl.
*A61C 8/00* (2006.01)
(52) U.S. Cl. ...................... 433/173; 174/175
(58) Field of Classification Search ............... 433/173
See application file for complete search history.

(56) References Cited
U.S. PATENT DOCUMENTS 6,227,859 B1 * 5/2001 Sutter .................. 433/173
6,854,972 B1 * 2/2005 Elian .................... 433/173
2003/0104337 A1  6/2003 Cottrell

FOREIGN PATENT DOCUMENTS

| EP | 0 599 794 A2 | 6/1994 |
| EP | 0 879 580 A2 | 11/1998 |
| WO | WO 01/50972 A2 | 7/2001 |

* cited by examiner

*Primary Examiner*—Cris Rodriguez
*Assistant Examiner*—Candice C Stokes
(74) *Attorney, Agent, or Firm*—Scully, Scott, Murphy & Presser, P.C.

(57) ABSTRACT

An intraosteal dental implant having a bone tissue apposition surface extending form a tip of the dental implant up to an interface at a neck portion of the dental implant, and a soft tissue apposition surface extending from the interface to a shoulder of the dental implant, wherein the shoulder is inclined with respect to the axis of the dental implant, and wherein preferably the shoulder is substantially contained in a plane.

14 Claims, 7 Drawing Sheets

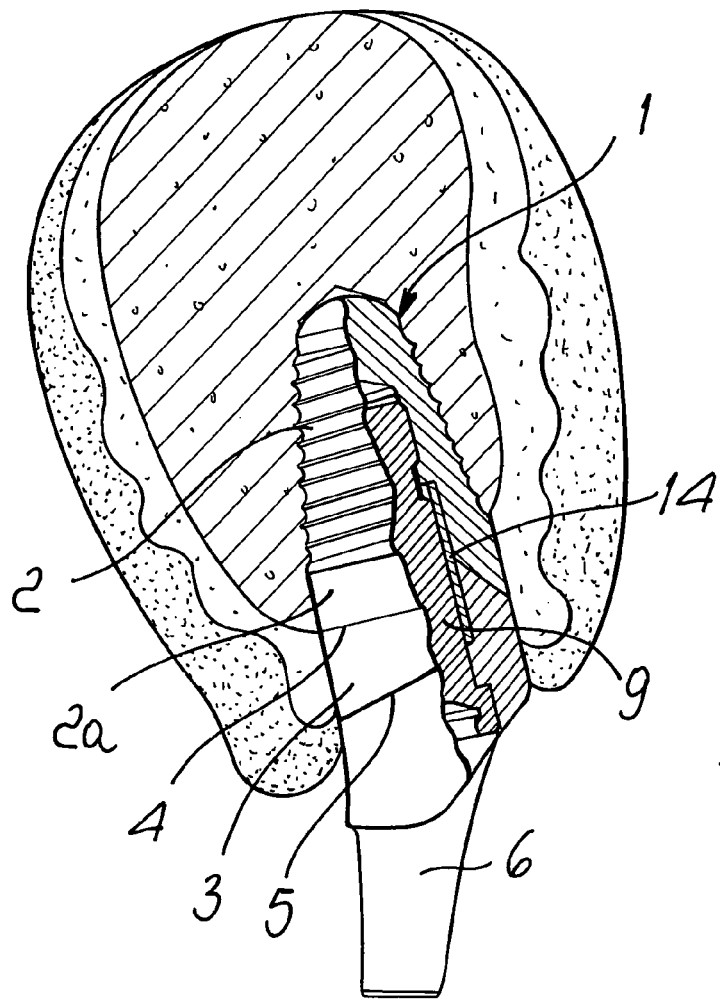
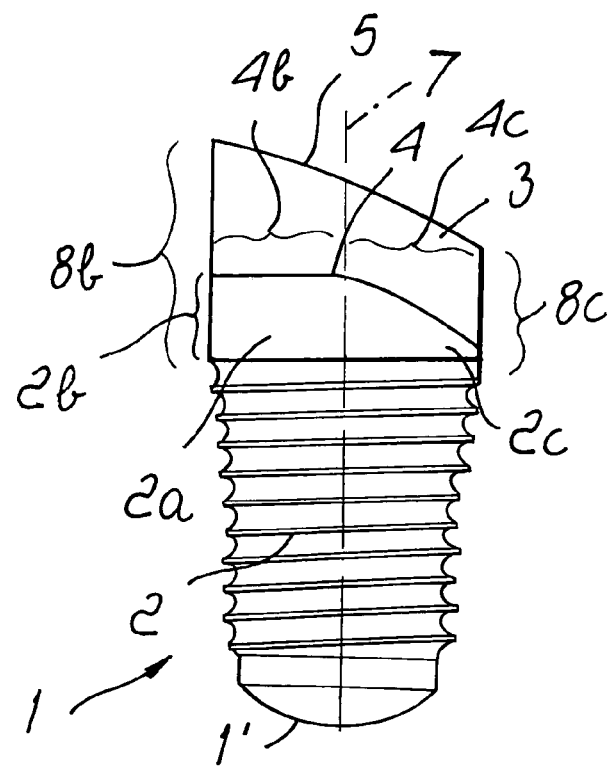

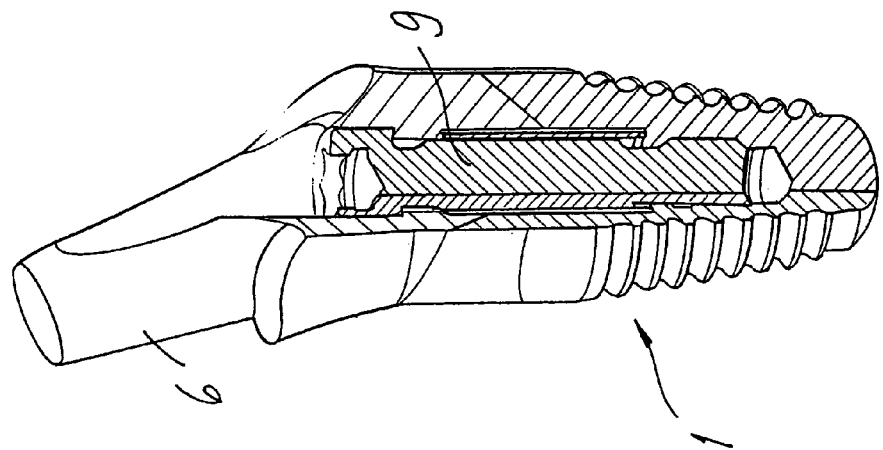
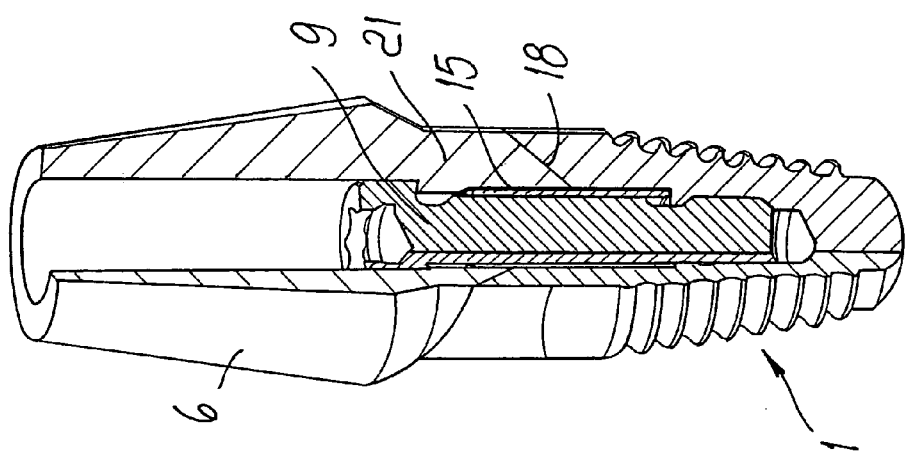
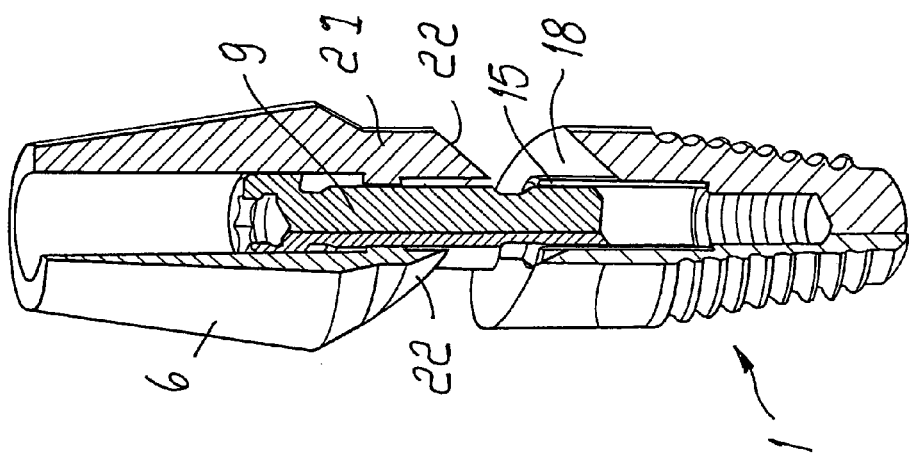

INTRAOSTEAL DENTAL IMPLANT

The present invention relates in general to an improved intraosteal dental implant and in particular to an intraosteal dental implant with an improved geometry of the soft tissue apposition surface.

BACKGROUND OF THE INVENTION

Intraosteal implants are widely used in dental restorations to support fixed or removable prostheses where the natural root of a teeth has been lost.

Schroeder et al. Oral Implantology, Georg Thieme Verlag Stuttgart and New York, $2^{nd}$ edition, 1996, p. 128, relates to an implant to be inserted transgingivally into a jaw bone having an apically extending shank portion, on which there may be an external thread, and which terminates at the very bottom with an implant tip. The shank portion is adjoined by an implant neck which terminates at the very top with an implant shoulder which conically tapers coronally. To favor osseointegration, an additive and/or non-additive surface structuring is provided on the implant, the surface extending over the shank portion to a horizontal structure boundary situated on the implant neck. Thus, the boundary defines an interface between a bone tissue apposition surface of the implant and a soft-tissue apposition surface of the implant.

Apart from the problem of setting boundaries for the surface structuring on the coronal implant neck, there is also the problem of not allowing the implant shoulder to be visible when the implants are set while also optimally supporting the surrounding jaw bone. For implants set to an adequate depth, various abutments with anatomically adapted shaping have been proposed (see for examples DE 195 34 979 C1, DE 196 07 427 A1, DE 196 20 394 C1, U.S. Pat. No. 5,417,568 and WO 99/02102). In the case of semisubmerged implants and especially transgingivally set implants, there is also the risk however of incomplete coverage of the implant shoulder and consequently of aesthetic impairment.

To alleviate the above problems WO-A-01 49199, which was assigned to the assignee of the present invention and the content of which is herewith fully incorporated by reference, has proposed an intraosteal dental implant with an anatomically suitable conformation for aesthetic restoration, in particular, in the front teeth region. The known implant comprises an additive or a non-additive surface structure, in order to favor osteal integration, the surface structure extending over the shank section up to a structure boundary or interface on the neck of the implant. The structure boundary falls anteriorly in the apical direction to a low point and rises, on the proximal implant edge, to a high point. The shoulder of the implant is anatomically formed to follow the boundary or interface such that, on the interdental side surfaces, raised regions exist and, on each of the anterior and posterior implant edges, recessed regions exist.

The above described prior art dental implants, however, are not readily accessible in the palatal or in the lingual area to the implantologist.

SUMMARY OF THE INVENTION

In view of the above it is an object of the invention to provide for an improved intraosteal dental implant which avoids the drawbacks of the prior art and which is readily accessible to the implantologist in particular in the palatal or lingual area, while still conforming with aesthetic requirements.

Another object of the present invention is to provide an abutment suitable for the dental implant of the present invention.

The foregoing objects as well as further objects which will become apparent hereinafter are achieved by the novel intraosteal dental implant as defined in the appended claims.

BRIEF DESCRIPTION OF THE DRAWINGS

The foregoing and other objects, features, and advantages of the invention, as well as presently preferred embodiments thereof, will become more apparent from a reading of the following description, in connection with the accompanying drawings in which:

FIG. 3C is a partially cut away interdental view of an intraosteal dental implant according to the third embodiment of the present invention in the implanted state thereof;

FIG. 4 is an interdental view of an intraosteal dental implant according to a fourth embodiment of the present invention; and FIGS. 5A through 7 show a preferred arrangement according to the present invention for the rotational positioning of an abutment into a dental implant.

DESCRIPTION OF THE PREFERRED EMBODIMENTS

Figure 1A:
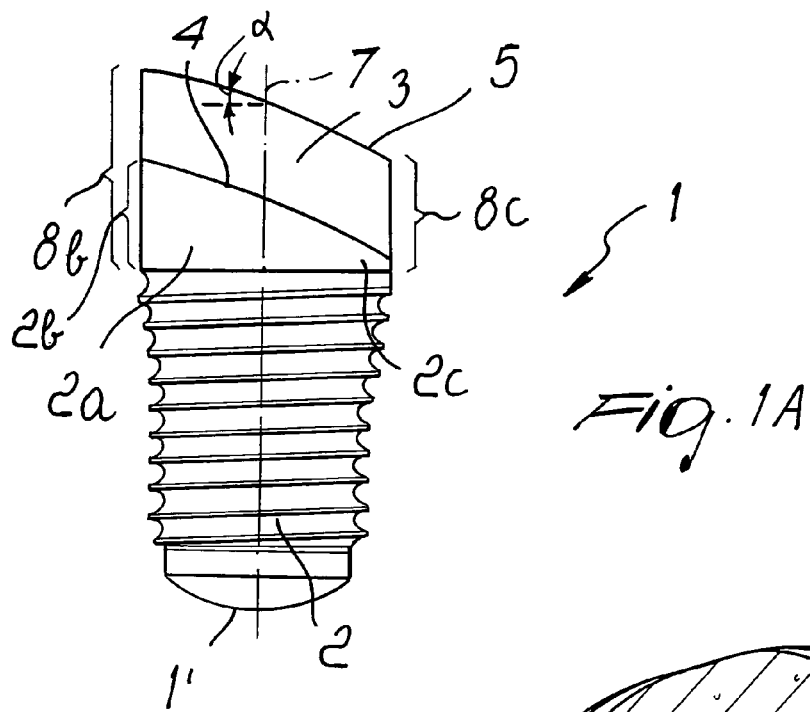
FIG. 1A is an interdental view of an intraosteal dental implant according to a first embodiment of the present invention.

As used in the following description and claims the terms lower/upper, left/right and vertical/horizontal are only intended for illustrative purposes and are by no means conceived to limit the scope of the invention.

According to the present invention, with reference to FIGS. 1A through 4, there is provided an intraosteal dental implant generally designated with reference numeral 1 with an apical tip 1'. The dental implant 1 has a bone tissue apposition surface 2 which is typically threaded and/or roughened in a known manner and extends into the alveolar bone in the inserted state of the dental implant. Although the shown dental implant has a screw like appearance, it will be appreciated by the person skilled in the art that other shapes like a root-like shape can be used without departing from the scope and spirit of the invention.

The coronal end of the bone apposition surface 2 defines a lower neck portion surface 2a. In addition the dental implant 1 is provided with a soft tissue apposition surface 3 extending from an upper end of the bone tissue apposition surface 2, at the neck portion surface 2a, up to a shoulder 5 of the dental implant 1. Thus, an interface 4 is defined between the bone tissue and soft tissue apposition surfaces. The soft tissue apposition surface 3 defines an upper neck portion of the dental implant 1. The upper neck portion surface 3 and the lower neck portion surface 2a define the neck of the dental implant 1.

As known in the art, the bone tissue apposition surface 2 may be provided with an additive or non-additive surface structure extending up to the interface 4 in order to enhance the osteal integration. Such structure surface is well known to the person skilled in the art of dental implantology and will not be further described (see for instance Ralf-J Kohal et al., "Wurzelanaloge Titaniumimplantate (Bio-Design-Implantate" für die Sofortimplantation—Das Re-Implant®-System", Implantologie 1996; 2: 99-115).

The soft tissue apposition surface or upper neck portion surface 3 is machined, for instance by polishing, to obtain a surface enhancing the regeneration and the attachment of the soft tissue. Again, the machining of the soft tissue apposition surface is known in the art (see for instance Ralf-J Kohal et al., "Wurzelanaloge Titaniumimplantate (Bio-Design-Implantate" für die Sofortimplantation—Das Re-Implant®-System", Implantologie 1996; 2: 99-115), and therefore the discussion thereof will be omitted in the present specification. Also the provision of additives for the soft tissue apposition surface, which is per se known in the art, is envisaged by the present invention. Furthermore, other machining techniques, in addition to polishing, are envisaged and applicable to the present soft tissue apposition surface.

According to the present invention the plane of the shoulder 5 is inclined with respect to the axis 7 of the implant 1. In view of the processing of the shoulder 5 by means of milling, grinding or drilling with a conical tool the plane of the shoulder 5 may have a slightly curved shape. This is in particular the case if the dental implant 1 is devised with an inner neck surface 18 as shown and explained in conjunction with FIG. 5A.

The inclination reflects the morphologic difference between the palatal or lingual sides on one hand and the labial side on the other hand with respect to the alveolar bone anatomy. In other words, as shown in FIGS. 1B, 2B and 3B, in that particular case, the palatal side 8b of the dental implant 1 has a larger extension than the labial side 8c thereof. Similar considerations apply for a lower jaw bone implant where the lingual side of the dental implant has a larger extension than that of the labial side thereof.

The inclined shoulder 5 of the present invention assures a neck palatal side 8b or a neck lingual side (not shown) which is higher than the neck labial side 8c.

Figure 1B:
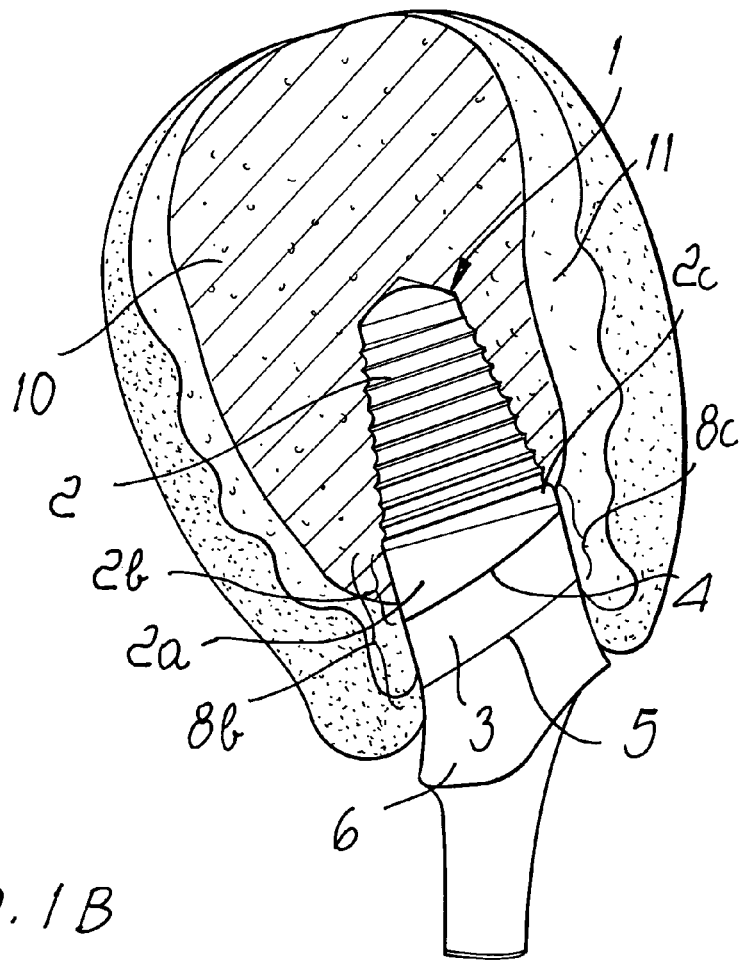
FIG. 1B is an interdental view of an intraosteal dental implant according to the first embodiment of the present invention in the implanted state thereof.

It has been found that the present invention shows particular advantages if the inclination of the plane of the shoulder 5 is in the range from about 10° to about 30° with respect to the plane perpendicular to the axis 7 of the implant 1, as indicated with α in FIG. 1A. In other words the inclination with respect to the axis 7 is in the range from about 60° to about 80°.

More preferred is the range from about 15° to about 25° with respect to the plane perpendicular to the axis 7 of the implant 1. In other words the more preferred inclination with respect to the axis 7 is in the range from about 65° to about 75°.

The most preferred inclination of the plane of the shoulder 5 is of about 20° with respect to the plane perpendicular to the axis 7 of the implant 1 or about 70° with respect to the axis 7.

Figure 1C:
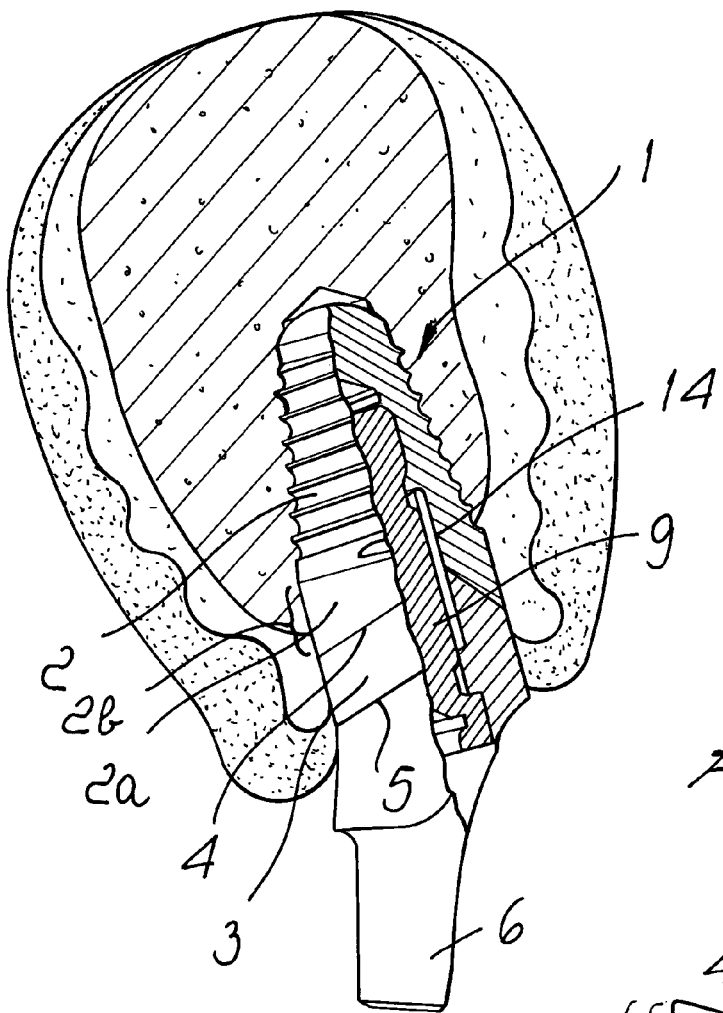
FIG. 1C is a partially cut away interdental view of an intraosteal dental implant according to the first embodiment of the present invention in the implanted state thereof.

FIGS. 1A through 1C show the implant according to the present invention wherein the interface 4 between the lower neck portion surface 2a and the soft tissue apposition surface 3 lays in a plane and extends substantially in a parallel manner to the shoulder 5 of the dental implant 1 which also lays in a plane. In other words, the plane passing through the interface 4 is parallel to the plane passing through the shoulder 5. Accordingly, the lower neck portion surface 2a has a palatal side 2b which has a larger extension than a labial side 2c thereof. Same applies for the ratio between the lingual side of the lower neck portion and the labial side thereof. It is believed that the first embodiment of the dental implant according to the present invention is particularly suitable for adjacent dental implants.

Preferably, the extension (width) of the soft tissue apposition surface 3 as defined by parallel interface 4 and shoulder 5 is in the range of about 0.5 to about 3 mm, and more preferred of about 1.8 mm.

FIG. 1B is an interdental view of an intraosteal dental implant 1 according to the present invention in the implanted state thereof. The dental implant 1 is located in the alveolar bone 10 which is schematically shown for explanatory purposes. The alveolar bone 10 is in contact with the soft tissue 11. According to FIG. 1B an abutment 6 can be apposed on the shoulder 5 of the dental implant 1. The abutment 6 is built to perfectly fit on the upper surface of shoulder 5 and to take into account the inclined shoulder 5 of the dental implant 1.

FIG. 1C further shows a section view of the dental implant 1 of the present invention. The section view shows a screw 9 located in a receiving bore 14 of the dental implant 1 which firmly fixes the abutment 6 to the dental implant 1. Furthermore, as described hereinafter, the abutment 6 may be advantageously provided in accordance with the present invention with a downwardly extending protrusion fitting into a respective receiving bore of the implant 1 such as to rotationally secure the latter element to another.

It has been noted that the dental implant according to the first embodiment of the present invention provides for particular advantages if implemented as a two stage implant.

Figure 2A:
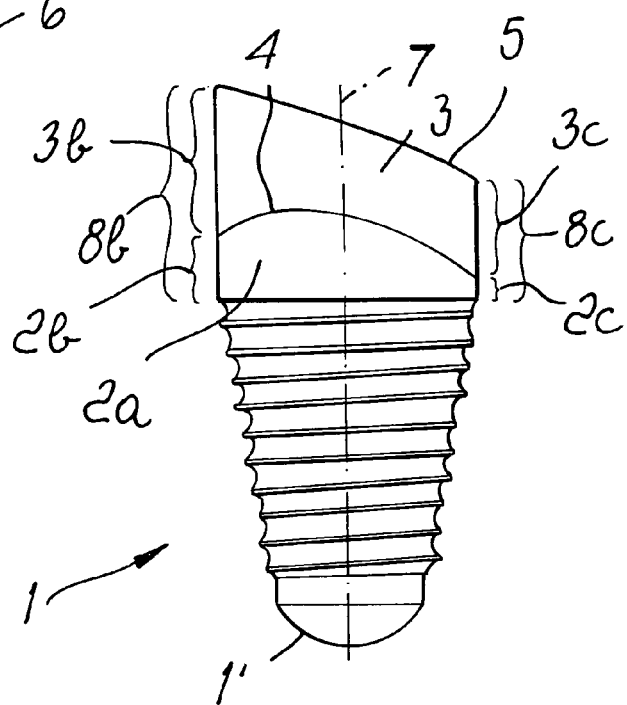
FIG. 2A is an interdental view of an intraosteal dental implant according to a second embodiment of the present invention.
Figure 2C:
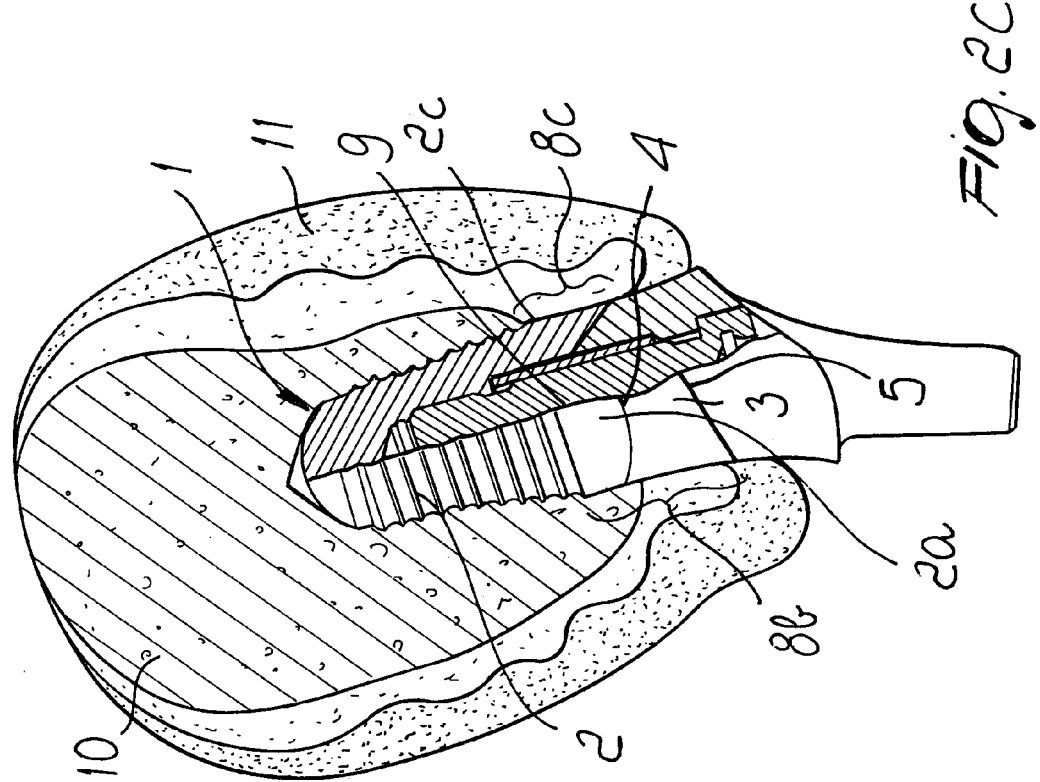
FIG. 2C is a partially cut away interdental view of an intraosteal dental implant according to the second embodiment of the present invention in the implanted state thereof.
Figure 2B:
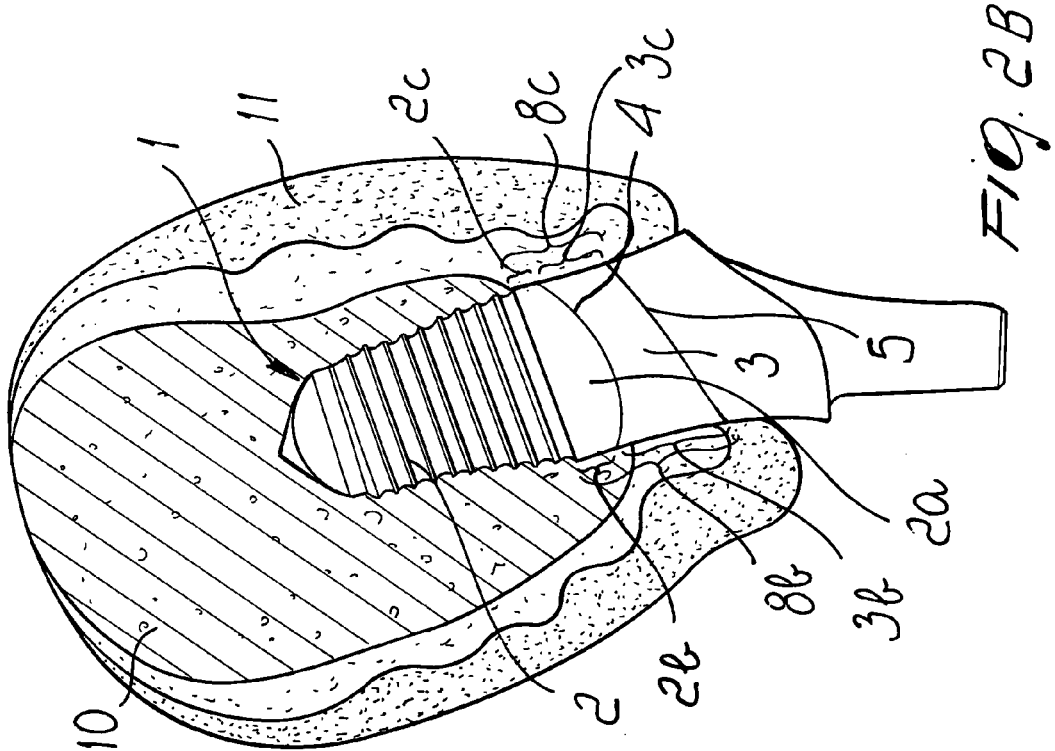
FIG. 2B is an interdental view of an intraosteal dental implant according to the second embodiment of the present invention in the implanted state thereof.

According to a second embodiment of the present invention as shown in FIG. 2A through FIG. 2C the interface 4 between the apposition surface 2a and the soft tissue apposition surface 3 has a curved profile similar to the interface (boundary) shown in WO-A-01 49 199. In particular, the curved profile of the interface 4 is such that it is increasing from the labial side towards the interdental side and decreasing towards the palatal/lingual side. The curved profile is designed to better reflect the bone-soft tissue profile around the cavity wherein the implant in intended to be located.

Preferably the extension (width) of the soft tissue apposition surface 3 as defined by the curved interface 4 is in the range of about 0.5 to about 3 mm, and more preferred of about 1.8 mm, at the labial side 3c, and in the range of about 0.5 to about 3 mm, and more preferred of about 2.8 mm, at the lingual/palatal side 3b.

Except for the curved profile of the interface 4 the second embodiment depicted in FIGS. 2A through 2C is the same as that of FIGS. 1A through 1C and therefore the same explanations as set forth in respect to the latter apply.

The inventors of the present invention surprisingly found that for predictable bone and soft tissue preservation the plane passing through the interface 4 must not be parallel to the plane passing through the shoulder 5. In particular, the second embodiment of the present invention is believed to provide for a good bone tissue preservation notwithstanding the fact that the sloping of the interface 4 does not necessarily follow the outline of the bone tissue.

Figure 3A:
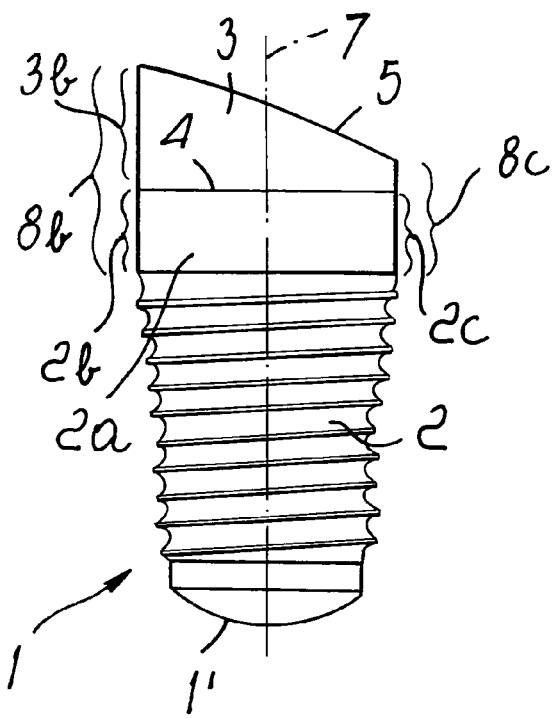
FIG. 3A is an interdental view of an intraosteal dental implant according to a third embodiment of the present invention.
Figure 3B:
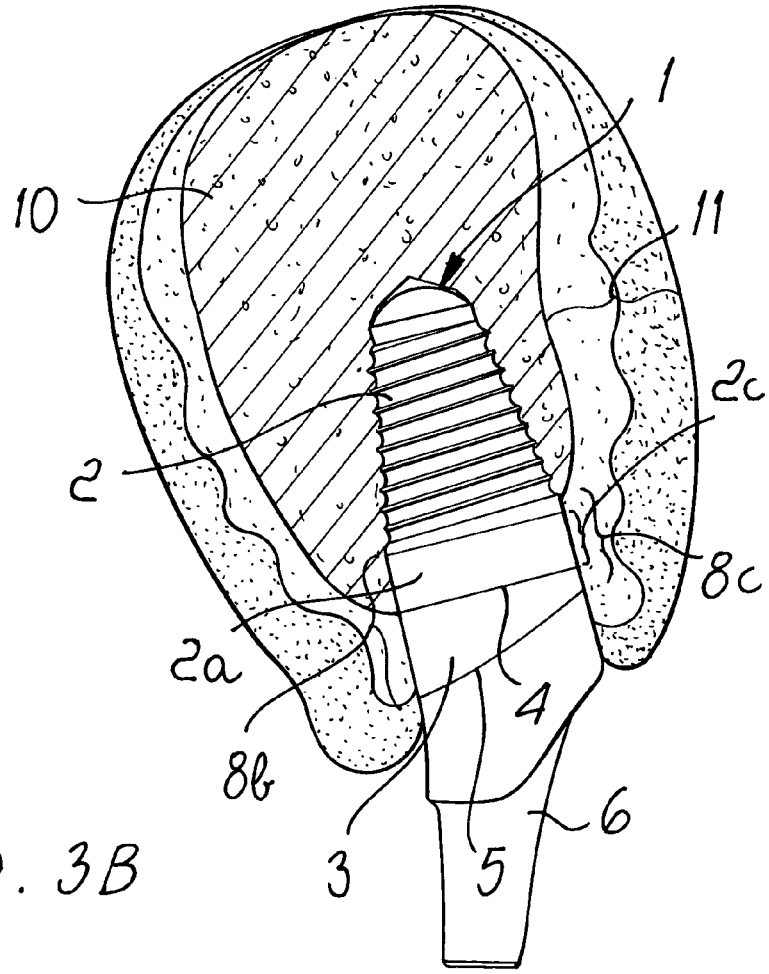
FIG. 3B is an interdental view of an intraosteal dental implant according to the third embodiment of the present invention in the implanted state thereof.

According to a third embodiment of the present invention, as shown in FIG. 3A through FIG. 3C, the interface 4 between the bone apposition surface 2 and the soft tissue apposition surface 3 lays in a plane substantially perpendicular to the axis 7 of the implant 1.

Preferably the extension (width) of the soft tissue apposition surface 3 as defined by the interface 4 perpendicular to the axis 7 of the dental implant 1 is in the range of about 0.5 to about 3 mm, and more preferred of about 2.3 mm at the palatal/lingual side 3b.

Except for the interface 4, which is substantially perpendicular to the axis 7 of the dental implant 1, the embodiment depicted in FIGS. 3A through 3C is the same as that of FIGS. 1A through 1C and therefore the same explanations as set forth in respect to the latter apply.

Again, in connection with the third embodiment of the present invention, the inventors surprisingly found that for predictable bone and soft tissue preservation the plane passing through the interface 4 must not be parallel to the plane passing through the shoulder 5. In fact, the third embodiment of the present invention is also believed to provide for a good bone tissue preservation notwithstanding the fact that the sloping of the interface 4 does not necessarily follow the outline of the bone tissue.

According to a fourth embodiment of the present invention as shown in FIG. 4 the palatal/lingual side 4b of the interface 4 between the bone tissue apposition surface 2 and the soft tissue apposition surface 3 lays in a plane which is substantially perpendicular to the axis 7 of the implant 1 and the labial side 4c of the interface 4 is curved. Basically, in the fourth embodiment the palatal/lingual side 4b of the interface 4 resembles to the corresponding side of the third embodiment while the the curved labial side 4c of the interface 4 resembles to the corresponding side of the second embodiment.

Except for the interface 4, which is as described above, the embodiment depicted in FIG. 4 is the same as that of FIGS. 1A through 1C and therefore the same explanations as set forth in respect to the latter apply.

In a similar manner to the third and second embodiments, the fourth embodiment of the present invention is believed to provide for a good bone tissue preservation notwithstanding the fact that the sloping of the interface 4 does not necessarily follow the outline of the bone tissue.

With reference to FIGS. 5A through 7 there is shown a preferred arrangement according to the present invention for the rotational positioning of the abutment 6 into the dental implant 1. The person skilled in the art will appreciate that the latter arrangement can be used in conjunction with all of the dental implants described above and also with further conventional prior art dental implants.

Figure 5A:
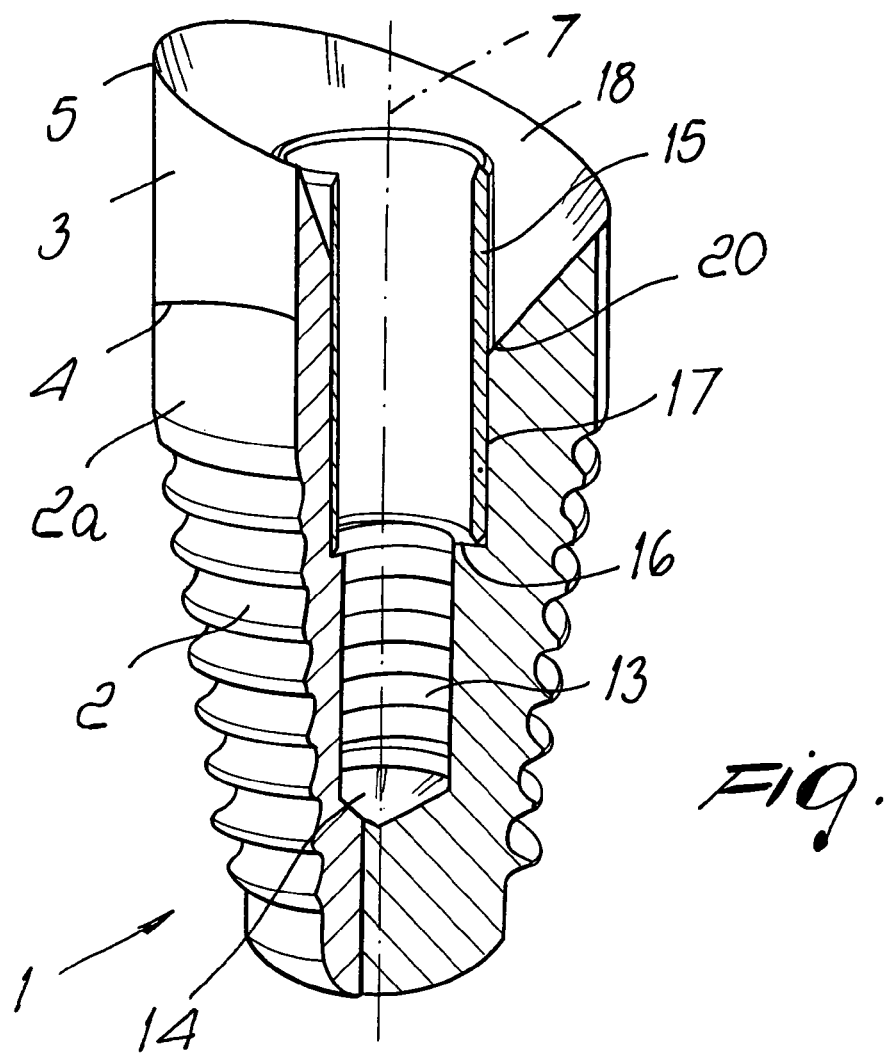

As shown in FIG. 5A, which is a perspective view of a partially cut away of a dental implant, the dental implant 1 according to the invention is provided in a conventional manner with a receiving bore 14 in the form of a blind hole having an internal thread 13 and which extends axially from coronal to apical. At the coronal end of the internal thread 13 of the receiving bore 14 there is provided a substantially circular rest surface 16 which extends in a perpendicular manner to the axis 7 of the implant and which receives substantially cylindrical sleeve 15. The sleeve 15 and the internal wall 17 of the bore 14 are sized such that the sleeve 15 precisely fits the internal wall 17. The sleeve 15 is fixedly retained in the space defined by the internal wall 17 and the rest surface 16.

Figure 5B:
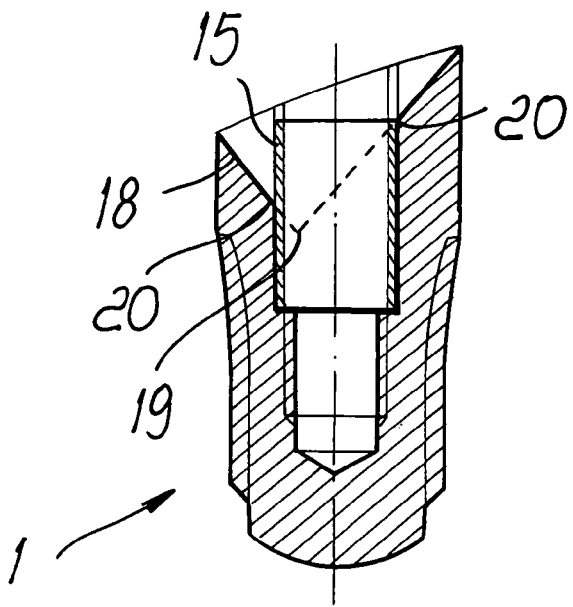

As shown in FIG. 5B, which is a sectional view of FIG. 5A, the inner neck surface 18 of the dental implant 1 defined below the shoulder 5 can have preferably a substantially conical shape with an imaginary tip 19 offset from the axis 7 of the dental implant 1. In this way, a complementary shaped abutment 6, as shown in FIGS. 6A through 7, can be accommodated between the sleeve 15 and the inner neck surface 18 such that the abutment 6 is rotationally secured to the dental implant 1. It is noted that the rotational securing can be achieved, for instance, by providing the intersection curve 20 between the inner neck surface 18 of the dental implant 1 and the sleeve 15 such that the intersection curve does not lay in a plane perpendicular to the axis 7 of the dental implant 1.

FIGS. 6A and 6B show a straight abutment 6 having a downwardly extending protrusion 21 with a lower surface 22 exactly matching the inner neck surface 18 of the dental implant 1. As shown in FIG. 6B, in the assembled state of the abutment, the downwardly extending protrusion 21 surrounds the sleeve 15 and the lower surface 22 rests on the inner neck surface 18. The screw 9 also fits the sleeve 15 with no or very little play to improve the stability of the arrangement. The thread pitch of the screw is preferably from 0.5 to 1.3 mm and more preferred from 0.5 to 0.8 mm in order to improve the positioning of the abutment.

FIG. 7 shows an arrangement similar to that of FIGS. 6A and 6B, wherein the abutment is inclined.

The foregoing description of the invention, including a preferred embodiment thereof, has been presented for the purpose of illustration and description. It is not intended to be exhaustive nor is it intended to limit the invention to the precise form disclosed. It will be apparent to those skilled in the art that the disclosed embodiments may be modified in light of the above teachings. In particular, a person skilled in the art will readily understand that the shape or outline of the interface between the soft tissue apposition surface and the bone tissue apposition surface may be variated.

The embodiments described are chosen to provide an illustration of principles of the invention and its practical application to enable thereby one of ordinary skill in the art to utilize the invention in various embodiments and with various modifications as are suited to the particular use contemplated. Therefore, the foregoing description is to be considered exemplary, rather than limiting, and the true scope of the invention is that described in the appended claims.

The disclosures in EPA No. 04007245.6 from which this application claims priority are incorporated herein by reference.

What is claimed is:

1. An intraosteal dental implant having a bone tissue apposition surface extending from a tip of the dental implant up to an interface at a neck portion of the dental implant, and a soft tissue apposition surface extending from the interface to a shoulder of the dental implant, wherein the shoulder is inclined with respect to the axis of the dental implant;

the neck portion of the dental implant has a palatal or lingual side, a labial side and an interdental side, the palatal or lingual side having a larger extension than the labial side; and the interface has a curved profile which is increasing from the labial side towards the interdental side and decreasing towards the palatal/lingual side.

2. An intraosteal dental implant having a bone tissue apposition surface extending from a tip of the dental implant up to an interface at a neck portion of the dental implant, and a soft tissue apposition surface extending from the interface to a shoulder of the dental implant,
   wherein the shoulder is inclined with respect to the axis of the dental implant;
   the neck portion of the dental implant has a palatal or lingual side, a labial side and an interdental side, the palatal or lingual side having a larger extension than the labial side; and
   the interface has a curved profile which is increasing from the labial side towards the interdental side of and a horizontal profile, substantially perpendicular to the axis from the interdental side towards the palatal/lingual side.

3. An intraosteal dental implant having a bone tissue apposition surface extending from a tip of the dental implant up to an interface at a neck portion of the dental implant, and a soft tissue apposition surface extending from the interface to a shoulder of the dental implant,
   wherein the shoulder is inclined with respect to the axis of the dental implant;
   the implant further comprises a bore in the form of a blind hole, the bore being shared and devised such as to rotationally secure an abutment receivable in the dental implant;
   the bore is provided with a substantially cylindrical sleeve extending coaxially to the dental implant;
   the dental implant includes an inner neck surface, and an intersection curve between the inner neck surface of the dental implant and the sleeve does not lay in a plane perpendicular to the axis of the dental implant.

4. The intraosteal dental implant of claim 3 in combination with an abutment, the abutment having a downwardly extending protrusion with a lower surface exactly matching the inner neck surface of the dental implant.

5. The combination of claim 4, wherein in the assembled state of the abutment, the downwardly extending protrusion surrounds the sleeve and the lower surface rests on the inner neck surface.

6. The combination of claim 5, further including a screw which fits into the sleeve with no or very little play.

7. The combination of claim 6, wherein the dental implant is a two stage implant.

8. The combination of claim 6, wherein the dental implant is an one stage implant.

9. An intraosteal dental implant having a bone tissue apposition surface extending from a tip of the dental implant up to an interface at a neck portion of the dental implant, and a soft tissue apposition surface extending from the interface to a shoulder of the dental implant,
   wherein the shoulder is inclined with respect to the axis of the dental implant;
   the implant further comprises a bore in the form of a blind hole, the bore being shaped and devised such as to rotationally secure an abutment receivable in the dental implant;
   the bore is provided with a substantially cylindrical sleeve extending coaxially to the dental implant; and
   the dental implant includes an inner neck surface, the inner neck surface of the dental implant having a substantially conical shape with an imaginary tip offset from the axis of the dental implant.

10. The intraosteal dental implant of claim 9 in combination with an abutment, the abutment having a downwardly extending protrusion with a lower surface exactly matching the inner neck surface of the dental implant.

11. The intraosteal dental implant of any one of claims 1, 2, 3 or 9 wherein the shoulder has an inclination in the range from about 60° to about 80°.

12. The intraosteal dental implant of claim 11, wherein the inclination of the shoulder is in the range from about 65° to about 75°.

13. The intraosteal dental implant of claim 12, wherein the inclination of the shoulder is about 70°.

14. The intraosteal dental implant of any one of claims 1, 2, 3 or 9 wherein the shoulder is substantially contained in a plane.

* * * * *